(12) United States Patent
Redmond et al.

(10) Patent No.: US 7,910,580 B2
(45) Date of Patent: *Mar. 22, 2011

(54) ENHANCEMENT OF EFFECTIVENESS OF 5-FLUOROURACIL IN TREATMENT OF TUMOR METASTASES AND CANCER

(75) Inventors: H. Paul Redmond, Cork (IE); Rolf W. Pfirrmann, Lucerne (CH)

(73) Assignee: Ed. Geistlich Soehne AG Fuer Chemische Industrie, Wolhusen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/016,294

(22) Filed: Jan. 18, 2008

(65) Prior Publication Data

US 2008/0114011 A1 May 15, 2008

Related U.S. Application Data

(60) Continuation of application No. 10/660,798, filed on Sep. 12, 2003, now Pat. No. 7,345,039, which is a continuation-in-part of application No. 10/281,138, filed on Oct. 28, 2002, now Pat. No. 6,815,441, which is a continuation-in-part of application No. 09/993,896, filed on Nov. 27, 2001, now abandoned, said application No. 10/281,138 is a division of application No. 09/583,902, filed on Jun. 1, 2000, now Pat. No. 6,479,481.

(60) Provisional application No. 60/253,138, filed on Nov. 28, 2000, provisional application No. 60/182,200, filed on Feb. 14, 2000, provisional application No. 60/174,607, filed on Jan. 5, 2000, provisional application No. 60/167,681, filed on Nov. 29, 1999, provisional application No. 60/151,050, filed on Aug. 27, 1999, provisional application No. 60/137,421, filed on Jun. 4, 1999.

(51) Int. Cl.
*A61K 31/54* (2006.01)
*A61K 31/505* (2006.01)

(52) U.S. Cl. ..................... 514/223.8; 514/274
(58) Field of Classification Search ............... 514/223.8, 514/274
See application file for complete search history.

(56) References Cited

U.S. PATENT DOCUMENTS

| | | | |
|---|---|---|---|
| 504,243 A | 8/1893 | Philippot |
| 1,039,140 A | 9/1912 | Kampfe |
| 1,188,697 A | 6/1916 | Steinberg |
| 1,461,366 A | 7/1923 | Mulford et al. |
| 1,676,146 A | 7/1928 | Krafft |
| 2,021,465 A | 11/1935 | Ritscher |
| 2,609,960 A | 9/1952 | Irwin |
| 2,643,024 A | 6/1953 | Cronheim |
| 2,760,672 A | 8/1956 | Cronheim |
| 3,598,105 A | 8/1971 | Cristaldi |
| 3,809,064 A | 5/1974 | Ziegler |
| 3,961,443 A | 6/1976 | Insalaco |
| 4,000,830 A | 1/1977 | French |
| 4,350,156 A | 9/1982 | Malchesky et al. |
| 4,467,784 A | 8/1984 | Lee et al. |
| 4,482,077 A | 11/1984 | Henderson |
| 4,626,536 A | 12/1986 | Pfirrmann |
| 4,654,345 A | 3/1987 | Cavanak |
| 4,828,140 A | 5/1989 | Henderson |
| 4,960,415 A | 10/1990 | Reinmüller |
| 5,077,281 A | 12/1991 | Reinmüller |
| 5,167,960 A | 12/1992 | Ito et al. |
| 5,176,651 A | 1/1993 | Allgood et al. |
| 5,191,900 A | 3/1993 | Mishra |
| 5,208,018 A | 5/1993 | Gough |
| 5,210,083 A | 5/1993 | Pfirrman et al. |
| 5,262,403 A | 11/1993 | Nicolson et al. |
| 5,362,754 A | 11/1994 | Raad et al. |
| 5,416,091 A | 5/1995 | King |
| 5,441,481 A | 8/1995 | Mishra et al. |
| 5,554,148 A | 9/1996 | Aebischer et al. |
| 5,593,665 A | 1/1997 | Pfirrman et al. |
| 5,725,553 A | 3/1998 | Moenning |
| 5,730,045 A | 3/1998 | Delaquis et al. |
| 5,749,859 A | 5/1998 | Powell |
| 5,763,421 A | 6/1998 | Caretto et al. |
| 5,819,748 A | 10/1998 | Pfirrmann |
| 5,881,905 A | 3/1999 | Brady |
| 5,889,183 A | 3/1999 | Herdeis et al. |
| 5,957,038 A | 9/1999 | Shimazaki |
| 6,011,030 A | 1/2000 | Pfirrmann |
| 6,029,843 A | 2/2000 | Kroscher et al. |

(Continued)

FOREIGN PATENT DOCUMENTS

CA 2302720 A1 9/2000

(Continued)

OTHER PUBLICATIONS

Bedrosian et al., "Taurolidine, an Analogue of the Amino Acid Taurine, Supresses Interleukin-1 and Tumor Necrosis Factor Synthesis in Human Peripheral Blood Mononuclear Cells", Cytokine 3(6), 1991, pp. 568-575.

(Continued)

*Primary Examiner* — James D Anderson
(74) *Attorney, Agent, or Firm* — Rothwell, Figg, Ernst & Manbeck, P.C.

(57) ABSTRACT

Tumor growth and metastases in cancer patients are inhibited by administration of a combination therapy including effective amounts of 5-Fluorouracil and a methylol transfer agent such as taurolidine, taurultam or mixtures thereof.

8 Claims, No Drawings

U.S. PATENT DOCUMENTS

| | | | |
|---|---|---|---|
| 6,030,358 A | 2/2000 | Odland | |
| 6,035,766 A | 3/2000 | Schirmer | |
| 6,080,397 A | 6/2000 | Pfirrmann | |
| 6,093,180 A | 7/2000 | Elsberry | |
| 6,105,811 A | 8/2000 | Alfred | |
| 6,117,868 A | 9/2000 | Pfirrmann | |
| 6,166,007 A | 12/2000 | Sodemann | |
| 6,258,797 B1 * | 7/2001 | Lehner | 514/56 |
| 6,303,596 B1 | 10/2001 | Morrissey et al. | |
| 6,429,224 B1 | 8/2002 | Calabresi et al. | |
| 6,479,481 B1 | 11/2002 | Stendel et al. | |
| 6,521,616 B2 | 2/2003 | Calabresi et al. | |
| 6,546,849 B1 | 4/2003 | Shimazaki | |
| 6,617,333 B2 | 9/2003 | Rabindran et al. | |
| 6,688,487 B2 | 2/2004 | Oakes et al. | |
| 6,815,441 B2 | 11/2004 | Stendel et al. | |
| 6,821,968 B2 | 11/2004 | Pfirrmann | |
| 6,995,164 B2 * | 2/2006 | Calabresi et al. | 514/263.32 |
| 7,151,099 B2 * | 12/2006 | Redmond et al. | 514/222.5 |
| 7,345,039 B2 | 3/2008 | Redmond et al. | |
| 2001/0031870 A1 | 10/2001 | Soll et al. | |
| 2002/0052366 A1 | 5/2002 | Calabresi et al. | |
| 2002/0091123 A1 | 7/2002 | Redmond et al. | |
| 2002/0098164 A1 | 7/2002 | Redmond et al. | |
| 2002/0111328 A1 | 8/2002 | Redmond et al. | |
| 2002/0111345 A1 | 8/2002 | Calabresi et al. | |
| 2002/0131935 A1 | 9/2002 | Fisher et al. | |
| 2003/0027818 A1 | 2/2003 | Redmond et al. | |
| 2003/0092707 A1 | 5/2003 | Redmond et al. | |
| 2003/0195198 A1 | 10/2003 | Stendal et al. | |
| 2004/0087579 A1 | 5/2004 | Redmond et al. | |

FOREIGN PATENT DOCUMENTS

| | | |
|---|---|---|
| CA | 2393159 A1 | 6/2001 |
| CA | 2393252 A1 | 6/2001 |
| CH | 587040 A5 | 4/1977 |
| DE | 3536560 A1 | 4/1986 |
| DE | 19606897 A1 | 8/1997 |
| EP | 0048558 A2 | 3/1982 |
| EP | 0139535 A2 | 5/1985 |
| EP | 0147021 A1 | 7/1985 |
| EP | 0253662 A1 | 1/1988 |
| EP | 1040841 A1 | 10/2000 |
| EP | 1 066 830 A2 | 1/2001 |
| EP | 1201247 A2 | 5/2002 |
| EP | 1247524 A1 | 10/2002 |
| GB | 2165752 A | 4/1986 |
| JP | 60-105618 A | 6/1985 |
| JP | 61-000017 A | 1/1986 |
| JP | 63-72626 A | 4/1988 |
| JP | 5-500973 | 2/1993 |
| JP | 5-505615 A | 8/1993 |
| JP | 2000-300661 A | 10/2000 |
| JP | 2000-516196 A | 12/2000 |
| JP | 2001-10976 A | 1/2001 |
| JP | 2002-326936 A | 11/2002 |
| WO | WO 88/05301 A1 | 7/1988 |
| WO | WO 91/13628 A1 | 9/1991 |
| WO | WO 92/00743 A1 | 1/1992 |
| WO | WO 95/18638 A1 | 7/1995 |
| WO | WO 95/30423 A2 | 11/1995 |
| WO | WO 97/25052 A2 | 7/1997 |
| WO | WO 98/28027 A1 | 7/1998 |
| WO | WO 98/39354 A1 | 9/1998 |
| WO | WO 98/52572 A1 | 11/1998 |
| WO | WO 99/06114 A2 | 2/1999 |
| WO | WO 00/01391 A1 | 1/2000 |
| WO | WO 01/39762 A2 | 6/2001 |
| WO | WO 01/39763 A2 | 6/2001 |
| WO | WO 02/07810 A2 | 1/2002 |

OTHER PUBLICATIONS

Braumann, et al., "The Influence of Intraoperative Intravenous and Intraperitoneal Application of Taurolidine with Heparin on Subcutaneous and Intraperitoneal Tumor Growth in Laparoscopic Surgery in a Rat Model", Department of Surgery, Humboldt—Univerity of Berlin, Campus Chartie Mitte, Schumannstra. 20-21, 10098 Berlin, Germany, Apr. 14 and 15, 2000, 3 pages, (Abstract Book).

Bruckner, et al., "Taurolin:, Ein neues Konzept zur antimikrobiellen Chemotherapie chirurgischer Infektionen", Urban & Schwarzenberg Munchen Wien Baltimore 1985, (English Summary attached).

Campbell, et al., "The Role of Tumor Rejection Antigens in Host Antitumor Defense Mechanisms" Cancer, Jun. 1, 1995, vol. 75, No. 11,, pp. 2649-2655.

Carter, et al., "Chemotherapy of Cancer", Scientific Library, Aug. 13, 1981, pp. 77-78.

Clarke et al., "KRN8602 (MX2-hydrochloride): An Active new Agent for the Treatment of Recurrent High-Grade Glioma", J. Clin Oncol, Aug. 1999, 17(8): 2579-84, (Abstract only).

Da Costa, et al. "Laparotomy and Laparoscopy Differentially Accelerate Experimental Flank Tumor Growth", British Journal of Surgery, 1998, 85, pp. 1439-1442.

Da Costa, et al., "The effect of Laparotomy and Laparoscopy on the Establishment of Spontaneous Tumor Metastases", Surgery, vol. 124, No. 3, Sep. 1998, pp. 516-525.

Dimmock et al., "Mannich Bases of Phenolic Azobenzenes Possessing Cytotoxic Activity", Eur. J. Med. Chem., vol. 32, 1997, pp. 583-594.

Erb, et al., "Structural Investigation of a New Organic Antiseptic: Taurolidine A Spectroscopic Study of Its Stability and Equilibria in Various Solvents", Talanta. 1982, vol. 29., 953-958.

Erb, et al., "Structural Investigation of a New Organic Antiseptic: Taurolidine Analytical Study and Application to Identification and Quantitation in Biological Fluids" European Journal of Drug Metabolism and Pharmacokinetics, 1983, vol. 8, No. 2, pp. 163-173.

Fanning, et al., "Inhibition of Neutrophil Apoptosis after Elective Surgery", Surgery, Sep. 1999, vol. 26, No. 3, pp. 527-534.

Finnegan, et al., "Cancer", Jan. 1, 1998, vol. 82, No. 1., pp. 186-199.

Foye et al., "ACS Professional Reference Book" Cancer Chemotherapeutic Agents, American Cancer Society, 1995, pp. 50-55.

Gallagher, et al., "Hepatic Resection of Solitary Metastasis From Transitional Cell Carcinoma of the Bladder", The Journal of Urology, Mar. 1998, vol. 159, p. 986.

Hansen et al., "Altretamine", DICP, The Annals of Pharmacotherapy, 1991, vol. 25, 146-152.

Hood, et al., "Studies of the Thiadiazine, Taurolidine-I. Indentification of the Molecular Species Present in Aqueous Solutions by $^1$H- and $^{13}$C-NMR Spectroscopy", Talanta, vol. 41, No. 1, pp. 107-113, 1994, pp. 107-113.

Jacobi et al., "Influence of Different Gases and Intraperitoneal Instillation of Antiadherent or Cytotoxic Agents on Peritoneal Tumor Cell Growth and Implantation with Laparoscopic Surgery in a Rat Model", Surg. Endosc, 1999, 13: 1021-1025.

Jacobi et al., Inhibition of Peritoneal Tumor Cell Growth and Implantation in Laparoscopic Surgery in a Rat Model, American Journal of Surgery, 174, Sep. 1997, pp. 359-363.

Jacobi et al., Intraperitoneal Installation of Taurolidine and Heparin for the Prevention of Intraperitoneal Tumor Growth and Trocar Metastases in Laparoscopic Surgery in a Rat Model, Langenbecks Arch Chir, 1997, 382 [Suppl 1]: S31-S36., "Abstract".

Jacobi et al., "New Therapeutic Strategies to Avoid Intra-and Extraperitoneal Metastases during Laparoscopy: Results of a Tumor Model in the Rat", Dig Surg, 1999; 16: 393-399.

McCourt et al., "Taurolidine Inhibits Tumor Cell Growth in Vitro and In Vivo", Annals of Surgical Oncology, 7(9): 2000; 685-691.

McNamara, et al., "Significance of Angiogenesis in Cancer Therapy", British Journal of Surgery, Mar. 9, 1998, 85, pp. 1044-1055.

Monson et al., Abrogation of Tumor Necrosis Factor (TNF) Toxicity in the Murine Model by Taurolidine: Support for Synergism of TNF with Endotoxin, Br. J. Surg., 77(6), Jun. 1990, A708.

Monson et al., Preliminary Evidence that Taurolidne is Antineoplastic as well as anti-endotoxin and anti-microbial, Br. J. Surg., 77(6), Jun. 1990, A711.

Monson et al., Taurolidine as an Anti-neoplastic Agent: A previously undiscovered Role?, Br. J. Surg., 77(12), Dec. 1990, 1432.

Monson et al., Taurolidine Inhibits Tumour Necrosis Factor (TNF) toxicity—New Evidence of TNF and Endotoxin Synergy, Euro. J. Surg. Oncology 1993; 19: 226-231.

Parfitt "Martindale, the complete drug reference, $32^{nd}$ ed", (formerly Martindale the extra pharmacopoeia), London: Pharmacopoeia), XP-002231711, London: Pharmaceutical press, GB, 534-537.

Pidgeon et al., "The Role of Endotoxin/Lipopolysaccharide in Surgically Induced Tumour Growth in a Murine Model of Metastatic", Bristish Journal of Cancer, 1999, 81(8), 1311-1317.

Redmond et al. Impact of CO2 and Gasless Laparoscopy as Well as Laparotomy on Peritoneal Tumour Growth and Abdominal Wall Metastases, Annals of Surgery, vol. 227, No. 2, p. 309.

Suzuki et al., Japanese Journal of Gastroenterological Surgery, May 1, 1994, vol. 27, 5, p. 1090-1093.

The Japanese Journal of Gastroenterological Surgery, vol. 23, No. 2, 1990, 3 pgs, (Abstract only).

The Japanese Journal of Gastroenterological Surgery, vol. 24, No. 2, 1991, 3 pgs.

The Japanese Journal of Gastroenterological Surgery, vol. 30, No. 6, 1997, 3 pgs.

Wang et al., "Endotoxin/Lipopolysaccharide Activates NF-kB and Enhances Tumor Cell Adhesion and Invasion Through a B1 Integrin-Dependent Mechanism", the Journal of Immunology, vol. 170, 2003, pp. 795-804.

Watson et al., "Taurolidine, an Antilipopolysaccharide Agent, has Immunoregulatory Properties that are Mediated by the Amiono Acid Taurine", Journal of Leukocyte Biology, vol. 58, Sep. 1995, pp. 299-306.

Weberschock "Efficacy of Sytemic Taurolidin Application in the Treatment of Liver Metastases in a Hat Model", Dept. of General and Vascular Surgery, Johann Wolfgang Goethe—University Franfurt/Main Germany, p. 41.

Wu et al., "Neutrophil-induced Transmigration of Tumour Cells Treated with Tumour-conditioned Medium is Facilitated by Granulocyte-macrophage Colony-stimulating Factor", Eur. J. Surg. 2000, 166: pp. 361-366.

Canadian Office Action from CA appln. No. 2,379,734 dated Sep. 29, 2008, 3 pages.

Japanese Office Action for JP appln 2002-280476 entitled "Preliminary Notice of Reasons for Rejection", Dec. 4, 2008, and English language translation, pp. 1-7.

European Search Report from EP appln. No. 01 30 9983 dated Apr. 9, 2003, 4 pages.

Ananthan, in Cancer Chemotherapeutic Agents, Foye (Ed.), American Chem. Soc., Washington, D.C. (1995) pp. 49-58.

Anderson et al., "The Role of cytokines, Adhesion Molecules, and Chemokines in Interleukin-2-induced Lymphocytic Infiltration in C57BL/6 Mice" J. Clin. Inv. 97: 1952-1959, 1996.

Anonymous, "Cerebrospinal Fluid" http://uscneurosurgery.com/infonet/glossary/c/cerebrospinal%20fluid%20csf.htm. 2 pages. Accessed May 31, 2007.

Anonymous, "Methods of Sterilisation." British Pharmacopoeia. vol. 2, Appendix XVIII: A264-A267, 1998.

Anonymous, "Taurolin Suppresses Activity of Tumor Necrosis Factor-α in vivo" Institute of Pharmacology, University of Zurich, Research Report, 1-9, 1993.

Araki et al., J. Jap. Soc. Gastroenterol. Surg. 27(5): 1090-1093, 1994.

Blenkharn, "The Antimicrobial Activity of Taurolin®—a Possible New Additive for Parenteral Nutrition Solutions" Clin. Nutr. 6(1): 35-38, 1987.

Blum et al., "Hexamethylmelamine—A New Drug with Activity in Solid Tumors" Eur. J. Cancer, 9:195-202, 1973.

Bobrich et al., "Influence of intraperitoneal application of taurolidine/heparin on expression of adhesion molecules and colon cancer in rats undergoing laparoscopy" J. Surg. Res. 137(1):75-82, 2007.

Braumann et al., "Influence of intraperitoneal and systemic application of taurolidine and taurolidine/heparin during laparoscopy on intraperitoneal and subcutaneous tumour growth in rats" Clin. Exp. Metastasis 18: 547-552, 2001.

Braumann et al., "Local and systemic chemotherapy with taurolidine and taurolidine/heparin in colon cancer-bearing rats undergoing laparotomy" Clin. Exp. Metastasis, 20: 387-394, 2003.

Braumann et al., "The Tumor-Suppressive Reagent Taurolidine Is an Inhibitor of Protein Biosynthesis" Int. J. Cancer, 112: 225-230, 2004.

Braumann et al., "Effects of increasing doses of a bolus injection and an intravenous long-term therapy of taurolidine on subcutaneous (metastatic) tumor growth in rats" Clin. Exp. Metastasis, 22: 77-83, 2005.

Braumann et al., "High Doses of Taurolidine Inhibit Advanced Intraperitoneal Tumor Growth in Rats", J. Surg. Res. 129: 129-135, 2005.

Braumann et al., "Prevention of disease progression in a patient with a gastric cancer-re-recurrence. Outcome after intravenous treatment with the novel antineoplastic agent taurolidine. Report of a case" World J. Surg. Oncol. 4(34): 6 pages, 2006.

Braumann et al., "The Tumor Suppressive Reagent Taurolidine Inhibits Growth of Malignant Melanoma—a Mouse Model" Journal of Surgical Research, vol. 143, (2007), pp. 372-378.

Calabresi et al., "Taurolidine: Cytotoxic and Mechanistic Evaluation of a Novel Antineoplastic Agent" Can. Res. 61: 6816-6821, 2001.

Da Costa et al., "Taurolidine Improves Survival by Abrogating the Accelerated Development and Proliferation of Solid Tumors and Development of Organ Metastases from Circulating Tumor Cells Released Following Surgery" J. Surg. Res. 101:111-119, 2001.

Darnowski et al., "Mechanistic and antineoplastic evaluation of taurolidine in the DU145 model of human prostate cancer" Can. Chemother. Pharmacol, 54: 249-258, 2004.

Edwards et al., "Pentoxifylline Inhibits Interleukin-2-induced Toxicity in C57BL/6 Mice but Preserves Antitumor Efficacy" J. Clin. Inv. 90: 637-641, 1992.

Endoh, "Effects of Recombinant Interleukin-2 (rIL-2) for Recurrent and Metastatic Renal Cell Carcinoma" Biotherapy, 5(6): 1100-1106, 1991.

Fiedler, in Lexikon der Hilfsstoffe für Pharmazie, Kosmetik und angrenzende Gebiete, Editio Cantor Aulendorf, 695, 1985.

Fukushima, "Merck Manual, $17^{th}$ Edition in Japanese" Nikkei BP, pp. 983-992, 1999 (partial English translation).

Gavrovskaya et al., "Antihypox Properties of Taurinamide Derivatives: The Experimental Study" Taurine, 6: 523-528, 2006.

Glesby et al., "Pilot Study of Low Dose Daily Interleukin-2 Plus Pegylated-Interferon-alfa-2b and Ribavirin in Patients with HCV/HIV Co-infection: ACTG A5088" $11^{th}$ Conf. Retrovir Opportunistic Infect., Abstract 818, 1-2, 2004.

Gugenheim et al., "Laparoscopic Resection of Solid Liver Tumours" Br. J. Surg., 83: 334-335, 1996.

Huscher et al., "Laparoscopic Colorectal Resection", Surg. Endosc. 10: 875-879, 1996.

Jacobi et al., "Taurolidine—a new drug with anti-tumor and anti-angiogenic effects", Anti-Cancer Drugs, 16(9): 917-921, 2005.

Jacobs et al. "Interleukin-2 or Autologous Lymphokine-activated Killer Cell Treatment of Malignant Glioma: Phase I Trial" Cancer Res. 46 (4 pt 2): 2101-2104,1986.

Janik et al., "Prevention of Postoperative Peritoneal Adhesions, Efficacy of Povidone", Arch Surg., 117: 1321-1324, 1982.

Johnston et al., "Taurolin for the Prevention of Parenternal Nutrition Related Infection: Antimicrobial Activity and Long-Term Use", Clin. Nutr. 12(6): 365-368, 1993.

Kilian et al., "Effects of taurolidine and octreotide on tumor growth and lipid peroxidation after staging-laparoscopy in ductal pancreatic cancer", Prostaglandins, Leukotrienes and Essential Fatty Acids, 69: 261-267, 2003.

Kilian et al., "Impact of taurolidin and octreotide on liver metastasis and lipid peroxidation after laparoscopy in chemical induced ductal pancreatic cancer", Investigational New Drugs, 23: 157-164, 2005.

Kimura et al., "A Phase III Randomized Study of Interleukin-2 Lymphokine-Activated Killer Cell Immunotherapy Combined with Chemotherapy or Radiotherapy after Curative or Noncurative Resection of Primary Lung Carcinoma" Cancer, 80: 42-49, 1997.

Kirsch et al., "The Effect of Polyvinylpyrrolidine on the Stability of Taurolidine", Pharm. Devel. and Tech., 2(4): 345-356. 1997.

Koike et al., "Effect of 48-hour Continuous Intravenous Injection of 5-Flouorouracil (5-FU) for Hematogenous Metastasis of Large Intestine Carcinoma", Jap. J. Gastro. Surg. 24(2): 1-3, 1991 (partial English translation).

Koldehoff et al., "Taurolidine is effective in the treatment of central venous catheter-related bloodstream infections in cancer patients", *Intl. J. Antimicrobial Agents*, 24: 491-495, 2004.

Kopple et al., "Effect of Intravenous Taurine Supplementation on Plasma, Blood Cell, and Urine Taurine Concentrations in Adults Undergoing Long-term Parenteral Nutrition[1-3]", *Am. J. Clin. Nutr.*, 52(5): 846-853, 1990.

Lubec et al., "Decreased Tumor Incidence and Increased Survival by One Year Oral Low Dose Arginine Supplementation in the Mouse" Life Sciences, 58(25): 2317-2325, 1996.

Lucarotti et al., "Antiseptic Toxicity to breast carcinoma in tissue culture an adjuvant to conservation therapy", *Ann. Roy. Coll. of Surg. of Eng.*, 72: 388-392, 1990.

Lung Cancer, The 38th Japan Lung Cancer Conference, The Japan Lung Cancer Society, 37(5):765, 1997.

Medical Encyclopedia: Electrolytes http://www.nlm.nih.gov/medlineplus/ency/article/002350.htm, 1, 2001. Accessed May 31, 2007.

Medical Encyclopedia: Protein in diet http://www.nlm.nih.gov/medlineplus/print/ency/article/002467.htm, 1-2, 2001. Accessed May 31, 2007.

Med. J. Kinki Univ., Kinki University Medical Conference, 25(1): 17A, 2000.

Monson, "Malignant Melanoma: A Plague of our Times", *Br. J. Surg.*, 76: 997-998, 1989.

Mughal et al., "Infected Feeding Lines", *Care Critically Ill* 6(6): 228-231, 1990.

Negrier et al., "Interleukin-2 with or without LAK Cells in Metastatic Renal Cell Carcinoma: A Report of a European Multicenter Study" *Eur. J. Cancer Clin. Oncol.* 25: suppl. 3 S21-S28, 1989.

Nestler et al., "Impact of taurolidine on the growth of CC531 colon carcinoma cells in vitro and in a laparoscopic animal model in rats", *Surg. Endosc.*, 19: 280-284, 2005.

Nici et al., "The Effects of Taurolidine, a Novel Antineoplastic Agent, on Human Malignant Mesothelioma", *Clin. Can. Res.* 10: 7655-7661, 2004.

Nudelman et al., "Prodrugs of butyric acid. Novel derivatives possessing increased aqueous solubility and potential for treating cancer and blood diseases", *Eur. J. Med. Chem.* 36: 63-74, 2001.

O'Brien et al., "Co-immunotherapy with interleukin-2 and taurolidine for progressive metastatic melanoma", *Irish J. Med. Sci.* 175(1): 10-15, 2006.

Okuno et al., "Intrahepatic interleukin-2 with chemotherapy for unresectable liver metastases: a randomized multicenter trial" *Hepato-Gastroenterology*, 46(26): 1116-21, Abstract, 1 pg., 1999.

Opitz et al., "The influence of adhesion prophylactic substances and taurolidine/heparin on local recurrence and intraperitoneal tumor growth after laparoscopic-assisted bowel resection of colon carcinoma in a rat model" Surg. Endosc. 17:1098-1104, 2003.

Opitz et al., "Instillation of Taurolidine/Heparin after Laparotomy Reduces Intraperitoneal Tumour Growth in a Colon Cancer Rat Model", *Eur. Surg. Res.* 39: 129-135, 2007.

Opitz et al., "Taurolidine and povidone-iodine induce different types of cell death in malignant pleural mesothelioma" Lung Cancer, 56: 327-336, 2007.

Opitz et al., "Local recurrence model of malignant pleural mesothelioma for investigation of intrapleural treatment", *Eur. J. Cardio-thoracic Surg.* 31: 772-778, 2007.

Physicians' Desk Reference, "Fluorouracil Product Information", pp. 2034-2036, 1995.

Reinmueller, "Die Beeinflussung der physiologischen und pathologischen Gerinnung durch Taurolidin und Implikationen für die Anwendung", *Zentralbl Chir Suppl*, 4: 13-18, 1999.

Reymond et al., "Feasibility of therapeutic pneumoperitoneum in a large animal model using a microvaporisator", *Surg. Endosc.*, 14: 51-55, 2000.

Ribizzi et al., "Taurolidine: preclinical evaluation of a novel, highly selective, agent for bone marrow purging", *Bone Marrow Transplantation*, 29: 313-319, 2002.

Rodak et al., "Induction of reactive oxygen intermediates-dependent programmed cell death in human malignant ex vivo glioma cells and inhibition of the vascular endothelial growth factor production by taurolidine", *J. Neurosurg.*, 102: 1055-1068, 2005.

Salmaggi et al., "Intrathecal immunotherapy in CNS tumors disseminating via CSF: preliminary evaluation using different treatment schedules" Italian Journal of Neurological Sciences, 17: 267-276, 1996.

Semple et al., "Potent and Selective Thrombin Inhibitors Featuring Hydrophobic, Basic $P_3$-$P_4$-aminoalkyllactam Moieties", *Bioorganic & Medicinal Chemistry Let.* 8: 3525-3530, 1998.

Shrayer et al., "The effect of Taurolidine on adherent and floating subpopulations of melanoma cells", *Anti-Cancer Drugs*, 14(4): 295-303, 2003.

Simon et al., "Diagnosis and treatment of catheter-related infections in paediatric oncology: and update", *Clin. Microbiol. Infect.*, 12(7): 606-620, 2006.

Smith, "Interleukin 2 Toxicity—Standard Procedures for Recording & Reporting Drug Toxicities", 1-8, 2000.

Smith et al., "New Strategies to Combat HIV: Augmenting Antiviral Immunity, Rationale for Low-Dose Daily IL-2 Therapy", *AIDS Read.* 13(8): 365-369, 382, 2003.

Stapleton et al., "Taurine and human nutrition", *Clin. Nutr.* 16(3):103-8, 1997.

Stapleton et al., "Taurine and Inflammation—A New Approach to an Old Problem?" *J. of Leukocyte Biol.*, 61: 231-232, 1997.

Stendel et al., "The Effect of Taurolidine on Brain Tumor Cells", *Anticancer Research*, 22: 809-814, 2002.

Stendel, R. et al., "Enhancement of fas-ligand-mediated programmed cell death by taurolidine", *Anticancer Research*, 23: 2309-2314, 2003.

Stendel et al., "Taurolidine-Fibrin-Sealant-Matrix Using Spray Application for Local Treatment of Brain Tumors", *Antican. Res.* 24: 631-638, 2004.

Stendel et al., "Treatment of Glioblastoma with Intravenous Taurolidine. First Clinical Experience", *Antican. Res.* 24: 1143-1148, 2004.

Stendel et al., "Pharmacokinetics of Taurolidine following Repeated Intravenous Infusions Measured by HPLC-ESI-MS?MS of the Derivatives Taurultame and Taurinamide in Glioblastoma Patients", *Clin. Pharmacokinet*, 46(6): 513-524, 2007.

Sun et al., "Taurolidine Induces Apoptosis of Murine Melanoma Cells in Vitro and In Vivo by Modulation of the Bcl-2 Family Proteins", *J. Sur. Oncol.* 96: 241-248, 2007.

Thatcher et al., "Recombinant interleukin-2 (rIL-2) given intrasplenically and intravenously for advanced malignant melanoma. A phase I and II study", *Br. J. Cancer*, 60: 770-774, 1989.

Treutner et al., "Prevention of Postoperative Adhesions by Single Intraperitoneal Medication", *J. Surg. Res.*, 59(6): 764-771, 1995.

University of Florida Shands Cancer Center: "Electrolyte Imbalance", http://www/ufscc.ufl.edu/Patient/content.aspx?section=ufscc&id-213137 (2006). Accessed May 4, 2006.

Van Gelder, "A Central Mechanism of Action for Taurine: Osmoregulation, Bivalent Cations, and Excitation Threshold", *Neurochem. Res.* 8(5): 687-699, 1983.

Volz,et al., "Modulation of Tumor-Induced Lethality after Pneumoperitoneum in a Mouse Model", *Cancer*, 89(2): 262-266, 2000.

Wakabayashi et al., "Chemotherapy for Brain Tumors", 50(2): 305-312, 2001.

Wenger et al., "Effects of taurolidine and octreotide on port site and liver metastasis after laparoscopy in an animal model of pancreatic cancer", *Clin. & Exp. Metastasis*, 19: 169-173, 2002.

Wittich et al., "Irrigation of Port Sites: Prevention of Port Site Metastases?" *J. Laparoendoscopic & Advanced Surg. Tech.* 14(3): 125-129, 2004.

Wördemann et al., "Tumor Necrosis Factor-α Production by Human Hepatoma Cell Lines Is Resistant to Drugs That Are Inhibitory to Macrophages", *J. Interf. and Cytokine Res.* 18: 1069-1075, 1998.

* cited by examiner

ENHANCEMENT OF EFFECTIVENESS OF 5-FLUOROURACIL IN TREATMENT OF TUMOR METASTASES AND CANCER

CROSS-REFERENCE TO RELATED APPLICATIONS

The present application is a continuation of pending U.S. application Ser. No. 10/660,798, filed Sep. 12, 2003, which is a continuation-in-part of U.S. application Ser. No. 10/281,138, filed Oct. 28, 2002, now U.S. Pat. No. 6,815,441, which is a continuation-in-part of U.S. application Ser. No. 09/993,896, filed Nov. 27, 2001, which claims the benefit of U.S. Provisional Application No. 60/253,138, filed Nov. 28, 2000. U.S. application Ser. No. 10/281,138 is a divisional of U.S. application Ser. No. 09/583,902, filed Jun. 1, 2000, now U.S. Pat. No. 6,479,481 B1, which claims the benefit of U.S. Provisional Application No. 60/182,200, filed Feb. 14, 2000, U.S. Provisional Application No. 60/174,607, filed Jan. 5, 2000, U.S. Provisional Application No. 60/167,681, filed Nov. 29, 1999, U.S. Provisional Application No. 60/151,050, filed Aug. 27, 1999 and U.S. Provisional Application No. 60/137,421, filed Jun. 4, 1999.

BACKGROUND OF THE INVENTION

1. Field of the Invention

The present invention relates to the field of treating tumor metastases and cancer.

2. Description of the Background Art

5-Fluorouracil (5-FU) is an antineoplastic drug with clinical activity in a variety of tumors, such as cancers of the colon and rectum, head and neck, liver, breast, and pancreas. One problem with 5-Fu is its extreme toxicity. Since 5-FU targets rapidly dividing cells, the primary toxic side effects are on bone marrow, intestinal mucousa and oral mucousa. Thus, leukocyte and platelet count decreases substantially after administration. Other side effects include stomatitis, diarrhea, nausea and vomiting. Neurological side effects include somnolence and ataxia. Other side effects include chest pain, myocardial necrosis and ischemia. Inflammatory reactions such as acute and chronic conjunctivitis leading to tear duct stenosis and ectropion also occur.

Monotherapy with 5-FU only results in tumor remission in about 20-25% of patients, and the average remission time is only about 6-8 months.

Although combination chemotherapy with 5-FU and other antineoplastic agents has been proposed, typically no substantive additional benefit is provided by the other antineoplastic agents over treatment with 5-FU alone.

Thus, there remains a significant need in the art for new and improved cancer treatment therapies.

SUMMARY OF THE INVENTION

In accordance with the present invention, tumor growth and metastasis is inhibited in a cancer patient by administering to said patient a combination therapy comprising effective amounts of 5-FU and a methylol transfer agent.

DETAILED DESCRIPTION OF THE INVENTION

It has surprisingly been found that methylol transfer agents such as taurolidine and taurultam substantially enhance or augment the antineoplastic effects of 5-FU in a combination therapy for inhibiting tumor metastases and treating cancer in patients. Such methylol transfer agents also substantially reduce the toxic side effects of 5-FU.

5-FU when used in accordance with the present invention includes biologically active derivatives or substantial equivalents thereof.

Methylol transfer agents include methylol-containing compounds such as taurolidine and taurultam. The compounds taurolidine and taurultam are disclosed in U.S. Pat. No. 5,210,083. Other suitable methylol-containing compounds may be found among those identified in PCT Publication No. WO 01/39763. Particularly preferred methylol transfer agents for utilization in accordance with the present invention are taurolidine, taurultam, biologically active derivatives thereof and mixtures thereof.

Particularly preferred embodiments involve treatment of cancers selected from the group consisting of colon cancer, rectal cancer and colo-rectal cancer, as well as inhibition of tumor metastases thereof.

Other cancers to which the combination therapy of the present invention is effective may include other carcinomas, sarcomas or lymphomas, cancers of the head and neck, liver cancer, breast cancer and pancreatic cancer. Cancers to which the present invention may be applicable include glioma, neuroblastoma, astrocytoma, carcinomatous meningitis, ovarian cancer, prostate cancer, central nervous system (CNS) cancer, lung cancer, gastric cancer, esophageal cancer, urinary bladder cancer, leukemia, lymphoma, melanoma, renal cell cancer and metastases thereof.

Effective daily dosage amounts of 5-FU may be in the range of about 0.1-1,000 mg per pharmaceutical dosage unit. Effective dosage amounts of 5-FU also may be in the range of about 100-5,000 mg/m$^2$ body surface area, preferably about 200-1,000 mg/m$^2$ body surface area, more preferably about 500-600 mg/m$^2$ body surface area. 5-FU typically is provided in 250 mg or 500 mg ampules for injection, or 250 mg capsules for oral administration.

Effective dosage amounts of a methylol transfer agent in accordance with the present invention may comprise pharmaceutical dosage units within the range of about 0.1-1,000 mg/kg. Preferred dosages may be in the range of about 10-20 grams taurolidine, taurultam or a mixture thereof, per administration.

Pharmaceutical dosage units of the combined therapy of the present invention may be administered by any suitable route, which include oral, topical or peritoneal administration, e.g., subcutaneously, intraperitoneally, intramuscularly, or intravenously, e.g., by infusion or injection.

In preferred embodiments, 250 ml of taurolidine 2% solution is administered by intravenous infusion about 1-6 times per day, more preferably about 2-4 times per day, during a treatment period, concurrently or sequentially with administration of 5-FU at a preferred dosage within the range of about 500-600 mg/m$^2$ body surface area. In accordance with one embodiment, 5-FU is administered by bolus intravenous injection at a dosage of 500 mg/m$^2$ body surface area, 1-3 days per week for a total of three weeks, during a treatment period including administration of taurolidine and/or taurultam. In an alternative embodiment, a 600 mg/m$^2$ intravenous bolus injection is administered 1-2 times per week during a three week treatment period, along with administration of taurolidine and/or taurultam as indicated above.

The present invention also is directed to a combination of 5-FU and a methylol transfer agent, in effective amounts for simultaneous, separate or sequential use for inhibiting tumor metastasis in a cancer patient. The invention also is directed to pharmaceutical combinations including pharmaceutical dosage units comprising effective amounts of 5-Fluorouracil and a methylol transfer agent for inhibiting tumor metastasis in a cancer patient, as well as to pharmaceutical compositions comprising such combinations.

In contrast with other antineoplastic agents, methylol transfer agents such as taurolidine and taurultam surprisingly and substantially enhance or augment the antineoplastic effects of 5-FU, and substantially reduce the extreme toxic side effects of 5-FU. Accordingly, with a combination therapy of 5-FU and a methylol transfer agent such as taurolidine and/or taurultam, the amount of 5-FU can be reduced to achieve the same activity as larger dosages of 5-FU alone, while encountering fewer toxic side effects. Alternatively, combination therapy in accordance with the present invention can be utilized with the same 5-FU dosage levels as monotherapy with 5-FU, while achieving enhanced antineoplastic results along with fewer side effects.

The invention is further illustrated by the following non-limiting example.

Example 1

The human colo-rectal cell lines SW 480 (primary), SW 620 (metastatic) and W 707 (metastatic) were incubated with the following: culture medium (control), taurolidine at 5, 10, 25, 50 and 100 µg/ml doses, and 5-Fluorouracil (5-FU) at 5, 10, 25, 50 and 100 µM doses. 5-FU was tested alone, and together with taurolidine. Cell proliferation, apoptosis and cell cycle were assessed.

There was a significant decrease in tumor cell proliferation at 24 hours. There was no significant increase in taurolidine-induced apoptosis and taurolidine did not alter the phases of the cell cycle. There was an increase in LDH release ($p=0.0011$), which correlated with inhibited tumor proliferation. Taurolidine was found to augment the effects of given doses of 5-FU ($p=0.0001$).

The invention claimed is:

1. A method of reducing toxic side effects of 5-fluorouracil (5-FU) antineoplastic therapy in a colon cancer, rectal cancer or colo-rectal cancer patient comprising administering to said patient effective amounts of a methylol transfer agent to substantially enhance the antineoplastic effects of 5-FU and to reduce the 5-FU dose needed to inhibit colon cancer, rectal cancer or colo-rectal cancer tumor growth and thereby reduce the toxic side effects of said 5-FU antineoplastic therapy, wherein said methylol transfer agent is taurolidine, taurultam or a mixture thereof.

2. The method of claim 1 wherein said tumor is colon cancer.

3. The method of claim 1 wherein said tumor is rectal cancer.

4. The method of claim 1 wherein said tumor is colo-rectal cancer.

5. The method of claim 1 wherein said tumor growth is metastatic tumor growth.

6. The method of claim 1 wherein said toxic side effects are selected from side effects on bone marrow, intestinal mucosa or oral mucosa, leukocyte or platelet count decreases, stomatitis, diarrhea, nausea, vomiting, neurological side effects, somnolence, ataxia, chest pain, myocardial necrosis, ischemia, inflammatory reactions, acute or chronic conjunctivitis, or tear duct stenosis or ectropion.

7. The method of claim 1 wherein said agent is administered at a dosage of about 0.1-1,000 mg/kg.

8. The method of claim 1 wherein said agent is administered at a dosage of about 10-20 grams.

\* \* \* \* \*